(12) United States Patent
Teckoe et al.

(10) Patent No.: US 9,504,654 B2
(45) Date of Patent: Nov. 29, 2016

(54) IMMEDIATE RELEASE FILM COATINGS CONTAINING MEDIUM CHAIN GLYCERIDES AND SUBSTRATES COATED THEREWITH

(71) Applicant: BPSI Holdings, LLC, Wilmington, DE (US)

(72) Inventors: Jason Teckoe, Lansdale, PA (US); Bradley J. Prusak, Hatfield, PA (US); Jeffrey R. Gimbel, Eagleville, PA (US); Daniel To, North Wales, PA (US)

(73) Assignee: BPSI HOLDINGS, LLC, Wilmington, DE (US)

( * ) Notice: Subject to any disclaimer, the term of this patent is extended or adjusted under 35 U.S.C. 154(b) by 0 days.

(21) Appl. No.: 14/597,025

(22) Filed: Jan. 14, 2015

(65) Prior Publication Data
US 2015/0202160 A1 Jul. 23, 2015

Related U.S. Application Data

(60) Provisional application No. 61/929,735, filed on Jan. 21, 2014.

(51) Int. Cl.
A61K 9/00 (2006.01)
A61K 9/28 (2006.01)

(52) U.S. Cl.
CPC .............. *A61K 9/282* (2013.01); *A61K 9/284* (2013.01); *A61K 9/2813* (2013.01); *A61K 9/2866* (2013.01)

(58) Field of Classification Search
CPC .... A61K 9/2813; A61K 9/282; A61K 9/284; A61K 9/2866
See application file for complete search history.

(56) References Cited

U.S. PATENT DOCUMENTS

| | | | |
|---|---|---|---|
| 4,497,847 A | 2/1985 | Kurihara et al. | |
| 4,543,570 A | 9/1985 | Bressert et al. | |
| 7,951,400 B2* | 5/2011 | Desai et al. | 424/472 |
| 8,388,983 B2 | 3/2013 | Farrell et al. | |
| 8,883,176 B2 | 11/2014 | Terzian et al. | |
| 8,900,606 B2 | 12/2014 | Hayashi et al. | |
| 2002/0103285 A1 | 8/2002 | Jordan et al. | |
| 2005/0152976 A1* | 7/2005 | Chenevier | A61K 9/2081 424/471 |
| 2005/0220878 A1 | 10/2005 | Fegely et al. | |
| 2006/0008533 A1* | 1/2006 | Habich | A23L 33/15 424/489 |
| 2008/0096979 A1* | 4/2008 | Pilgaonkar | A61K 9/5015 514/783 |
| 2008/0181928 A1 | 7/2008 | Hakimi-Mehr et al. | |
| 2010/0291159 A1 | 11/2010 | Farrell et al. | |
| 2010/0291183 A1 | 11/2010 | Farrell et al. | |
| 2013/0095141 A1* | 4/2013 | Schad | A23B 9/14 424/400 |
| 2015/0132374 A1* | 5/2015 | Coulter et al. | 424/472 |

FOREIGN PATENT DOCUMENTS

WO 2010122583 10/2010
WO WO 2014096983 A1 * 6/2014

OTHER PUBLICATIONS

Augngst. Intestinal Permeation Enhancers. J. Pharm. Sci. 2000, 89(4):429-442.*
Prajapati, et al., A Comparative Evaluation of Mono-,Di- and Triglyceride . . . , Pharm Res, vol. 29, pp. 285-305, 2012.
International Search Report issued in PCT Application No. PCT/US15/11422.

* cited by examiner

Primary Examiner — Robert A Wax
Assistant Examiner — Olga V Tcherkasskaya
(74) Attorney, Agent, or Firm — Lucas & Mercanti, LLP

(57) ABSTRACT

The present invention is directed to immediate release film coating compositions for use on oral dosage forms such as compressed tablets and other orally-ingestible substrates which contain medium chain glycerides as detackifiers. The film coating compositions can be applied either directly to a substrate or after the substrate has been coated with a subcoat. In preferred aspects, the polymer is polyvinyl alcohol and the medium chain glycerides are mixtures of caprylic (8 carbon chain) and capric (10 carbon chain) mono- and diesters of glycerin. Aqueous suspensions comprising the inventive film coating compositions, methods of applying the coatings to substrates and the coated substrates themselves are also disclosed.

19 Claims, No Drawings

IMMEDIATE RELEASE FILM COATINGS CONTAINING MEDIUM CHAIN GLYCERIDES AND SUBSTRATES COATED THEREWITH

CROSS-REFERENCE TO RELATED APPLICATIONS

This application claims the benefit of priority from U.S. Provisional Application Ser. No. 61/929,735, filed Jan. 21, 2014, the contents of which are incorporated herein by reference.

1. FIELD OF THE INVENTION

The present invention relates to immediate release film coating formulations which contain medium chain glycerides as detackifiers. The invention also relates to pharmaceutical substrates having such film coatings and methods of preparing the same.

2. BACKGROUND OF THE INVENTION

The use of detackifiers in film coating compositions is described in the prior art for both immediate release and enteric film coating applications. Commonly assigned U.S. Pat. No. 8,388,983 describes film coating formulations, which comprise fine particle size detackifiers that are practically insoluble in water. These detackifiers are in solid form at room temperature, alone, as part of a film coating formulation, and when dispersed in water. While film coatings containing these fine particle size detackifiers have many advantages such as good moisture barrier and high productivity, occasional aesthetic issues have been observed when using these coatings. The practically water-insoluble, fine particle size detackifiers may be present in logos on dosage forms or may be observed as specks on tablet surfaces, especially when the color of the coating is dark.

Accordingly, there is still a need for improved film coating compositions which have the advantages of good moisture barrier properties and high productivity. The present invention addresses this need.

3. SUMMARY OF THE INVENTION

It has been surprisingly found that immediate release film coating formulations comprising medium chain glycerides as detackifiers are well-dispersed in ambient temperature water and, when coated onto pharmaceutical compositions, completely disintegrate in less than two hours in both simulated gastric and intestinal fluids. Use of the inventive film coatings on oral substrates such as tablets results in improved product appearance, for example, in terms of reduced amounts of visible specks, as well as comparable or better moisture barrier performance of formulated coating systems when compared to that of the prior art.

The present invention relates to the development of fully-formulated film coating systems containing medium chain glycerides as detackifiers. The invention further relates to aqueous dispersions comprising the medium chain glycerides, methods of preparing the same by dispersing the film coating materials (system) in ambient temperature water and orally ingestible substrates having the inventive film coating comprising the medium chain glycerides dried thereon.

In one aspect of the invention, there are provided powder film coating compositions for the pharmaceutical and related arts. The preferably dry powder film coating compositions include one or more polymers, such as polyvinyl alcohol (hereinafter sometimes abbreviated as "PVA"), medium chain glycerides as detackifiers and optionally plasticizers, glidants, pigments and other additives commonly used in film coating formulations. In preferred aspects of this invention, the medium chain glycerides comprise a mixture of caprylic (8 carbon chain) and capric (10 carbon chain) mono- and diesters of glycerin.

In another aspect of the invention, there are provided aqueous dispersions of the film coating compositions described above that are prepared in ambient temperature water. The dispersions preferably contain from about 5 to about 40% non-water ingredients content. Still further aspects include methods of coating orally-ingestible substrates with the coating suspension as well as the coated substrates prepared by these methods.

In the preferred aspects of this invention, immediate release film coatings are prepared that completely disintegrate within 2 hours in both simulated gastric and intestinal fluids when coated onto orally-ingestible substrates in the amounts (weight gains) described herein. Furthermore, the coated ingestible substrates have low levels of visible specks on the surfaces of the coated orally-ingestible substrates, particularly in debossed or intagliated regions which may contain logos or the like. This combination of properties for an immediate release film coating system is clearly advantageous over the prior art and existing marketed products.

4. DETAILED DESCRIPTION OF THE INVENTION

For purposes of the present invention, the following terms are given further clarification as to their meanings:

"orally-ingestible substrate" shall be understood to mean any pharmaceutically acceptable dosage form, e.g. tablet, capsule, caplet, etc. or any other veterinary or confectionary product intended to be swallowed;

"dry powder" shall be understood to mean powders which are relatively dry to the touch rather than powders which are essentially without liquid content;

"ambient temperature" shall be understood to mean temperatures generally in the range of from about 20° C. (68° F.) to about 30° C. (86° F.)+/−3° C.;

"glycerin" is synonymous with "glycerol", and "glycerol esters" is synonymous with glycerides;

"simulated gastric fluids" are media having a pH from about 1 to about 5.5, which may be buffered or unbuffered, with or without enzymes; and "simulated intestinal fluids" are media having a pH from about 5.5 to about 8, which may be buffered or unbuffered, with or without enzymes.

The inventive film coating compositions comprise one or more polymers, medium chain glycerides and optionally glidants, pigments, surfactants or other film coating auxiliaries.

The polymer may be any of the commonly used immediate release film formers in the film coating art. These may include hypromellose (hydroxypropyl methylcellulose), hydroxypropyl cellulose, sodium carboxymethyl cellulose, polyvinyl alcohol (PVA), and copolymers based on PVA. A preferred grade of PVA is one prepared by hydrolyzing 86.5 to 89 mol % of the acetate groups on polyvinyl acetate. PVA copolymers may include PVA-polyethylene glycol graft copolymers such as those sold under the KOLLICOAT IR trade name or PVA-methyl methacrylate-acrylic acid copolymers such as those sold under the POVACOAT trade name. In some aspects, the polymers are of sufficiently small particle size, preferably less than 250 microns, to facilitate dissolution into ambient water when forming the aqueous coating solutions. Two or more of these polymers may be used together. PVA is a preferred polymer for many aspects of the invention.

In most embodiments, the amount of polymer included in the powder mixtures of the present invention is from about 20 to about 70% by weight. In some preferred embodiments, it ranges from about 25 to about 60% and more preferably ranges from about 30 to about 50%. When two or more polymers are used together, the combined total of the polymers is from about 20 to about 70% by weight. Also, when two or more polymers are used, the preferred total amount of polymers is from about 25 to 60% and more preferably from about 30 to about 50%.

The medium chain glycerides may be monoesters, diesters and triesters of glycerin with saturated aliphatic carboxylic acids having from 6 to 10 carbon atoms. Examples of such acids include straight chain acids such as hexanoic acid, heptanoic acid, octanoic acid (also known as caprylic acid), nonanoic acid and decanoic acid (also known as capric acid) as well as branched aliphatic carboxylic acids with a total carbon content of 6 to 10 atoms. The most preferred monoesters, diesters and triesters of glycerin remain in the liquid state at ambient temperatures. When a diester or triester of glycerin is employed, the carboxylic acid moieties on each molecule may be the same or different. Mixtures of esters, which may be monoesters, diesters and or triesters with different carboxylic acids, may also be employed.

In general, carboxylic acid esters of glycerin are mixtures of the monoester, diester and triester. Monoesters and diesters are preferred due to the presence of hydroxyl groups as will be explained later. Often, when preparing esters of glycerin, the mono-, di- and triesters are formed together. The relative ratio of the esters will depend upon the manufacturing conditions and the proportion of reagents. Triesters may be removed from the mixture, but it is often not economically practical from a manufacturing standpoint to completely remove all traces of the triester. Therefore, many commercial monoester and diester products contain a low level of triesters- for example, up to 10% by weight, i.e. 90% by weight mono and diesters of glycerin.

Likewise, in many cases, there may be small amounts of unreacted glycerin (up to about 10%) in commercial monoester and diester products. The presence of glycerin at these low levels does not appreciably affect the properties of the mono- and diesters. Medium chain glycerides may also contain small amounts (up to 10% by weight) of higher molecular weight esters of glycerin without adversely affecting their properties. These may include carboxylic acids having 11-18 carbon atoms. It is preferred that the medium chain glycerides remain in the liquid state at ambient temperatures.

In most preferred aspects of the invention, the medium chain glycerides comprise a mixture of caprylic (8 carbon chain) and capric (10 carbon chain) mono- and diesters of glycerin. Glycerol monocaprylocaprates are preferred. Glycerol monocaprylocaprate Type I as listed in the European Pharmacopoeia (EP) is one such example and is available under the trade name, Imwitor 742, from Cremer Oleo, GmbH and Co. KG, Hamburg, Germany. Alternative suppliers include Abitec, of Columbus Ohio with products available under the trade names Capmul MCM, EP and Capmul MCM, NF. Glycerol monocaprylocaprate Type I comprises 45-75% monoesters, 20-50% diesters, less than 10% triesters and less than 3% free glycerin. The carbon chain distribution is 50-90% C8 (or 8 carbons), 10-50% C10, less than 3% C12 and less than 1% C14. Another preferred glycerol monocaprylocaprate comprises 49-61% monoesters and 7% or less of free glycerin.

The medium chain glycerides are primarily used as detackifiers to reduce the incidence of tablet-to-tablet sticking that can occur during the film coating of pharmaceutical tablets and the like using aqueous suspensions/dispersions based on the inventive compositions. While not wishing to be bound by any particular theory, it is believed that the mono- and diesters function well as detackifiers for the polymers, because they possess both free hydroxyl groups and carboxylic acid esters. The hydroxyl groups on the medium chain glycerides can form hydrogen bonds with the hydroxyl groups on the polymer chains, while the more hydrophobic ester groups act as barriers to limit extensive association between polymer chains. Both mechanisms work together to prevent intermolecular associations between polymer chains that would otherwise lead to tackiness. The total amount of the medium chain glyceride detackifier present in the dry powder mixture will depend upon need, but can broadly range from about 1 to about 30% by weight. Preferably, the range is from about 2 to about 15% and more preferably from about 3 to about 7% by weight.

A glidant is optionally used to help tablets flow over each other and so generate a smooth surface finish. Talc and kaolin are preferred glidants. Preferred grades of talc have 90% of constituent particles less than 50 microns to eliminate the presence of visible specks on the surface of coated, orally-ingestible substrates. More preferred grades of talc have 90% of constituent particles less than 20 microns to further reduce the presence of visible specks and also to enhance dispersion properties. The amount of glidant, when present, will depend upon need, but can broadly range from about 1 to about 50% by weight. Preferably, the range is from about 4 to about 40%, and, more preferably, from about 10 to about 35%.

Pigments are also optionally added and may be any food or pharmaceutically approved colors, opacifiers or dyes. For example, the pigments may be aluminum lakes, iron oxides, titanium dioxide, natural colors or pearlescent pigments (e.g. mica based pigments sold under the Candurin trade name). Examples of such pigments are listed in U.S. Pat. No. 4,543,570, which is incorporated herein by reference. When included, the pigments may be used in the powder mixtures in a range (by weight) from about greater than 0 to about 40% pigment, preferably, from about 4 to about 32% and, more preferably, from about 7 to about 30%. It will be understood, however, that the amount of pigment employed in the powder mixtures of the invention is an amount which is sufficient or effective to impart the required appearance of the outer coating to the surface of the substrate to be coated.

Furthermore, the powder mixtures may also include supplemental or auxiliary ingredients typically found in film coatings. A non-limiting list of such adjuvants includes surfactants, suspension aids, sweeteners, flavorants, plasticizers etc. and mixtures thereof. Preferred surfactants are sodium lauryl sulfate and polysorbate 80. Sodium lauryl sulfate is a more preferred surfactant. The surfactant may be included in the range of about 0.1 to about 5% in the dry film coating composition, and, more preferably between about 1 to about 4%. The use and function of the surfactant is to enhance the film formation process as commonly taught and used in the prior art.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. Addition of liquids such as the medium chain glycerides will occur such that no significant agglomeration or separation will occur. This can be accomplished by gradually adding the liquid medium chain glycerides to the dry ingredients while blending. A preblend may also be utilized, wherein the liquid medium chain glycerides are first added to a portion of the dry ingredients and then the remaining dry material is added. The preblend may be prepared in bulk and used as needed to reduce the mixing time required for smaller batches. In all cases, when the liquid medium chain glycerides are added to the dry ingredients, the components must be mixed for a time sufficient to ensure homogeneity.

As mentioned above, batch sizes will vary upon need. A non-limiting list of suitable blending devices include diffusion blenders such as a cross flow, V-blender, or hub blenders, available from Patterson-Kelly, or convection blenders, such as Ruberg/Azo, Readco/CVM or Servolift blenders may be used. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

Some preferred dry film coating compositions in accordance with the invention include:

| Ingredient | % by weight | Preferred | More Preferred |
|---|---|---|---|
| Polymer (or polymers) e.g. PVA | 20-70 | 25-60 | 30-50 |
| Medium chain glycerides e.g. Glycerol mono-caprylocaprate Type I | 1-30 | 2-15 | 3-7 |
| Glidant e.g. talc, etc. | 0-50 | 4-40 | 10-35 |
| Surfactant e.g. Na lauryl sulfate, etc. | 0-5 | 1-4 | — |
| Pigments | 0-40 | 4-32 | 7-30 |
| Optional or aux. ingredients | 0-20 | — | — |

It will be understood from the foregoing table that the preferred dry film coating compositions will include at least a polymer and a medium chain glyceride as described herein. The additional ingredients, if included, will cause the amount of polymer and medium chain glyceride to be reduced proportionally but both components will still be within the ranges described herein, so that the total amount of all ingredients in the dry blend will be 100% by weight.

For purposes of illustration and not limitation, an aqueous dispersion having about 20% non-water ingredients can be formed by dispersing 100 grams of a blended powder mixture described hereinabove into 400 grams of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 100 grams of dry film coating composition is added to the vortex at a rate where there is no excessive buildup of dry powder. The speed and depth of the mixing blade is adjusted to avoid air being drawn into the suspension so as to avoid foaming. The suspension is stirred at low speed, preferably 350 rpm or less, for a time sufficient to ensure that a homogenous mixture is formed. Using the above batch size as a guide, about 45 minutes mixing time is required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used. It is contemplated that suitable aqueous dispersions will contain from about 5 to about 40% and preferably from about 15 to about 35% non-water ingredients therein.

In still further embodiments of the invention, there are provided orally-ingestible substrates coated with the inventive film coating formulations. The coated substrates have excellent appearance and uniformity as well as enhanced stability in the presence of environmental moisture and oxygen.

As will be described in the examples below, the methods include applying the film coating compositions as aqueous suspensions to the surfaces of orally ingestible substrates. The film coating can be applied as part of a pan coating or spray coating process commonly used to coat such articles. The amount of coating applied will depend upon several factors, including the nature and functionality of the film coating, the substrate to be coated and the apparatus employed to apply the coating, etc. In some immediate release applications of the invention, the substrates will be tablets and will be coated to a theoretical weight gain of from about 0.25 to about 5.0%. Preferably, the theoretical weight gain is from about 1.0 to about 4.5% and more preferably, the theoretical weight gain is from about 2.0 to about 4.0% by weight of said substrate. As mentioned above, the coating solutions of the present invention may also include auxiliary ingredients in addition to the powder mixture and the water.

The coated, orally-ingestible substrates described above can also include a subcoat film coating between the orally-ingestible substrate and the inventive film coating comprising medium chain glycerides. The subcoat selected is preferably based on an edible film coating composition that is compatible with and adheres to both the orally-ingestible substrate and the inventive coating. Thus, the artisan may choose from a wide variety of pharmaceutical or food-acceptable coatings for use as subcoats in the present invention. The subcoat is also applied to the substrate to provide from about a 0.25 to about a 5.0% weight gain to the orally-ingestible substrate.

Regardless of the method employed or the specific materials included in the film coating compositions, the orally-ingestible substrates of the present invention will include a polymer and medium chain glycerides.

5. EXAMPLES

The following examples serve to provide further appreciation of the invention but are not meant in any way to restrict the effective scope of the invention. All ingredients are expressed as being by weight %.

Example 1

A preferred formulation for an inventive dry coating composition is the following:

| Component | Parts by Weight |
|---|---|
| PVA | 37.0 |
| Talc | 31.0 |
| Glycerol monocaprylocaprate | 4.0 |
| Sodium lauryl sulfate | 3.0 |
| Titanium dioxide | 20.0 |
| Blue#2 aluminum lake pigment | 5.0 |
| | 100.0 |

Preparation of the Dry Film Coating Composition:

The dry film coating composition was prepared by adding all dry ingredients (PVA, talc, sodium lauryl sulfate and titanium dioxide) into a laboratory blender and blending for 5 minutes until a homogenous mixture was produced. Glycerol monocaprylocaprate, the only liquid component, was then gradually added to the dry mixture, and the total mixture was blended for an additional 2 minutes after all liquid was introduced.

Preparation of the Aqueous Dispersion:

The dry film coating composition (100 grams) was dispersed into 400 grams of ambient temperature water to make an aqueous coating suspension having 20% w/w non-water ingredients. The water was weighed into a vessel with a diameter approximately equal to the depth of the final dispersion. A low shear mixer was lowered into the water and turned on to create a vortex from the edge of the vessel down to just above the mixing blade to prevent entrapment of air. The 100 grams of dry film coating composition was added to the vortex at a rate where there was no excessive buildup of dry powder or foam. The speed and depth of the mixing blade was adjusted to avoid air being drawn into the suspension so as to avoid foaming. The suspension was stirred at low speed (350 rpm or less) for 45 minutes to form a homogeneous aqueous dispersion suitable for coating.

Coating of Tablets:

A 2.5 kilogram batch of convex placebo tablets (10 mm diameter) was spray coated with the aqueous dispersion described above in an O'Hara LabCoat fully perforated side-vented coating pan equipped with a pan insert having a diameter of 15" and one spray gun fitted with a nozzle having an aperture of 1 mm. The average coating parameters were: inlet temperature (IT) 76° C., exhaust temperature (ET) 48° C., coating bed temperature (BT) 45° C., airflow 297 cubic meters/hr., differential pressure −0.1 in. of water, atomizing air pressure (AP) 1.4 bar, pan speed (PS) 18 rpm. No tablet-to-tablet or tablet-to-coating pan sticking was observed at a spray rate of 30 grams/minute. A theoretical coating weight gain of 4.0% was applied to the tablets. The resulting coated tablets were smooth, non-tacky and glossy.

Determination of Moisture Vapor Transmission Rate:

Moisture vapor transmission rate (MVTR) was determined by first preparing a cast film sample from the aqueous dispersion described above by sequentially spraying the dispersion onto a flat polyethylene terephthalate (PET) surface secured on a metal plate heated to 60° C. A 100 micron thick film was thus obtained for testing. MVTR of the film was measured on a Mocon PermaTran-W 1/50 unit where the sample was tested at an 80% RH gradient at 25° C. The MVTR for the cast film prepared from the formulation of Example 1 was 95 grams $H_2O$/day/$m^2$.

Visual Assessment of Coated Tablets:

100 randomly selected tablets were carefully observed for the presence of small white specks. Only 9 out of 100 tablets had at least one very small speck on the tablet surface. No logo filling was observed.

Disintegration Test:

Disintegration testing was performed in accordance with the USP Disintegration Method. Six tablets were prepared as described previously and placed in a basket assembly and immersed in either simulated gastric fluid (0.1N HCl, pH 1.2), or simulated intestinal fluid (pH 6.8 phosphate buffer). The basket was moved up and down at a rate of about 28-32 cycles/minute. The integrity of the tablets was evaluated throughout the testing period, and the time for the first and last tablet to disintegrate noted. These values were then used to determine the average disintegration time for the samples in each media. The average disintegration time of the tablets in 0.1N HCl and pH 6.8 phosphate buffer was 86 and 93 seconds, respectively.

Comparative Example A

A formulation similar to that in Example 1 was prepared except that the glycerol monocaprylocaprate was eliminated from the formulation, and the talc level was increased to compensate.

| Component | Parts by Weight |
|---|---|
| PVA | 37.0 |
| Talc | 35.0 |
| Glycerol monocaprylocaprate | 0.0 |
| Sodium lauryl sulfate | 3.0 |
| Titanium dioxide | 20.0 |
| Blue#2 aluminum lake pigment | 5.0 |
| | 100.0 |

The aqueous dispersion preparation and coating process were conducted in an analogous fashion as that described in Example 1. The formulation did not disperse well in the aqueous medium, and significant foaming was observed. 20-25 tablets were observed to be stuck to the inside of the coating pan per revolution as the coating was being applied at a spray rate of 30 grams/minute. 100 out of 100 tablets showed the presence of visible specks on the tablet surface, and logo filling was observed Examples 2-12

Film coating compositions (100 grams each) and aqueous dispersions comprising them were prepared by methods similar to those described in Example 1. Coating performance and tablet properties were similarly assessed.

| Example | 2 | 3 | 4 | 5 | 6 |
|---|---|---|---|---|---|
| Component | % | % | % | % | % |
| PVA | 37.0 | 37.0 | 30.0 | 33.0 | 41.0 |
| Talc | 33.0 | 29.0 | 38.0 | 35.0 | 27.0 |
| Glycerol monocaprylocaprate | 2.0 | 6.0 | 4.0 | 4.0 | 4.0 |
| Sodium lauryl sulfate | 3.0 | 3.0 | 3.0 | 3.0 | 3.0 |
| Titanium dioxide | 20.0 | 20.0 | 20.0 | 20.0 | 20.0 |
| Blue#2 aluminium lake pigment | 5.0 | 5.0 | 5.0 | 5.0 | 5.0 |
| Totals | 100 | 100 | 100 | 100 | 100 |
| Performance | | | | | |
| Number of tablets stuck to coating pan per revolution at a spray rate of 30 grams/minute | 3-4 | 0 | 0 | 0 | 1 |
| Moisture vapor transmission rate of films (grams $H_2O$/day/$m^2$) | 94 | 141 | 78 | 83 | 108 |

-continued

| Example | 2 | 3 | 4 | 5 | 6 |
|---|---|---|---|---|---|
| Number of tablets showing white specks (out of 100) | 67 | 11 | 26 | 21 | 14 |
| Disintegration time (seconds) of coated tablets | | | | | |
| Simulated gastric fluid | 92 | 96 | 70 | 73 | 83 |
| Simulated intestinal fluid | 87 | 83 | 92 | 94 | 78 |

Examples 2-6 all showed that both the number of tablets showing white specks and the number of tablets sticking to the inside of the coating pan decreased significantly versus Comparative Example A. The greatest improvements were observed when the amount of glycerol monocaprylocaprate was at least 4% of the composition.

| Example | 7 | 8 | 9* | 10 |
|---|---|---|---|---|
| Component | % | % | % | % |
| PVA | 37.0 | 37.0 | | 26.0 |
| Hypromellose (6 cP viscosity) | | | 37.0 | |
| Hypromellose (15 cP viscosity) | | | | 11.0 |
| Talc | 34.0 | 28.0 | 31.0 | 31.0 |
| Glycerol monocaprylocaprate | 4.0 | 4.0 | 4.0 | 4.0 |
| Sodium lauryl sulfate | 0.0 | 6.0 | 3.0 | 3.0 |
| Titanium dioxide | 20.0 | 20.0 | 20.0 | 20.0 |
| Blue#2 aluminium lake pigment | 5.0 | 5.0 | 5.0 | 5.0 |
| Totals | 100 | 100 | 100 | 100 |
| Performance | | | | |
| Number of tablets stuck to coating pan per revolution at a spray rate of 30 grams/minute | 1-2 | 1 | 0 | 1-2 |
| Moisture vapor transmission rate of films (grams $H_2O$/day/$m^2$) | 82 | 75 | 171 | 71 |
| Number of tablets showing white specks (out of 100) | 35 | 10 | 21 | 10 |
| Disintegration time (seconds) of coated tablets | | | | |
| Simulated gastric fluid | 88 | 89 | 88 | 76 |
| Simulated intestinal fluid | 94 | 91 | 79 | 97 |

*Due to viscosity limitations, the aqueous dispersion made from Example 9 contained 15 rather than 20% non-water components.

Examples 7-10 all showed that both the number of tablets showing white specks and the number of tablets sticking to the inside of the coating pan decreased significantly versus Comparative Example A. This held true when the surfactant (sodium lauryl sulfate) level was varied and the polymer type was changed.

| Example | A restated | 11 | 12 |
|---|---|---|---|
| Component | % | % | % |
| PVA | 37.0 | 37.0 | 37.0 |
| Talc | 35.0 | 32.5 | 30.0 |
| Glycerol monocaprylocaprate | | 4.0 | 4.0 |
| Sodium lauryl sulfate | 3.0 | | |
| Polysorbate 80 | | 1.5 | 4.0 |
| Titanium dioxide | 20.0 | 20.0 | 20.0 |
| Blue#2 aluminium lake pigment | 5.0 | 5.0 | 5.0 |
| Totals | 100 | 100 | 100 |
| Performance | | | |
| Number of tablets stuck to coating pan per revolution at a spray rate of 30 grams/minute | 20-25 | 1-2 | 4-5 |
| Moisture vapor transmission rate of films (grams $H_2O$/day/$m^2$) | 92 | 86 | 153 |
| Number of tablets showing white specks (out of 100) | 100 | 16 | 8 |
| Disintegration time (seconds) of coated tablets | | | |
| Simulated gastric fluid | 95 | 88 | 87 |
| Simulated intestinal fluid | 105 | 102 | 94 |

Examples 11 and 12 showed that both the number of tablets showing white specks and the number of tablets sticking to the inside of the coating pan decreased significantly versus Comparative Example A when the surfactant type was changed.

| Example | 13 | 14 | 15 |
|---|---|---|---|
| Component | % | % | % |
| Kollicoat IR (PVA-PEG graft copolymer) | 37.0 | 68.0 | 64.0 |
| Talc | 31.0 | 0.0 | 4.0 |
| Glycerol monocaprylocaprate | 4.0 | 4.0 | 4.0 |
| Sodium lauryl sulfate | 3.0 | 3.0 | 3.0 |
| Titanium dioxide | 20.0 | 20.0 | 20.0 |
| Blue#2 aluminium lake pigment | 5.0 | 5.0 | 5.0 |
| Totals | 100 | 100 | 100 |
| Performance | | | |
| Number of tablets stuck to coating pan per revolution at a spray rate of 30 grams/minute | 0 | 1 | 1 |
| Moisture vapor transmission rate of films (grams $H_2O$/day/$m^2$) | 126 | 397 | 326 |
| Number of tablets showing white specks (out of 100) | 35 | 0 | 0 |
| Disintegration time (seconds) of coated tablets | | | |
| Simulated gastric fluid | 261 | 324 | 333 |
| Simulated intestinal fluid | 314 | 332 | 341 |

Examples 13-15 showed that both the number of tablets showing white specks and the number of tablets sticking to the inside of the coating pan decreased significantly versus Comparative Example A when the polymer was changed from PVA to Kollicoat IR and glycerol monocaprylocaprate was used as the detackifier.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. An immediate release film coating composition in powder form consisting essentially of a) a polymer selected from the group consisting of hypromellose (hydroxypropyl methylcellulose), hydroxypropyl cellulose, sodium carboxymethyl cellulose, polyvinyl alcohol, copolymers based on polyvinyl alcohol, and mixtures thereof b) a detackifier selected from the group consisting of medium chain glycerides containing less than or equal to about 10% by weight of triesters of glycerin, and c) a member of the group consisting of glidants, pigments, surfactants and mixtures thereof.

2. The immediate release film coating composition of claim 1, wherein the polymer is polyvinyl alcohol, copolymers based on polyvinyl alcohol or a mixture of polyvinyl alcohol and copolymers based on polyvinyl alcohol.

3. The immediate release film coating composition of claim 1, wherein the medium chain glycerides comprise a mixture of caprylic (8 carbon chain) and capric (10 carbon chain) mono- and diesters of glycerin.

4. The immediate release film coating composition of claim 3, wherein the medium chain glycerides comprise glycerol monocaprylocaprate or glycerol monocaprylocaprate Type I.

5. The immediate release film coating composition of claim 1, wherein the surfactant is sodium lauryl sulfate.

6. The immediate release film coating composition of claim 1, wherein the glidant is talc or kaolin.

7. The immediate release film coating composition of claim 1, wherein the polymer comprises 20-70% by weight of the composition.

8. The immediate release film coating composition of claim 1, wherein a) the polymer is polyvinyl alcohol, b) the medium chain glycerides comprise glycerol monocaprylocaprate, c) the glidant is talc, and d) the surfactant is sodium lauryl sulfate.

9. The immediate release film coating composition of claim 1, wherein the medium chain glycerides comprise from about 1 to about 30% by weight of the composition.

10. The immediate release film coating composition of claim 9, wherein the medium chain glycerides comprise from about 2 to about 15% by weight of the composition.

11. The immediate release film coating composition of claim 10, wherein the medium chain glycerides comprise from about 3 to about 7% by weight of composition.

12. An aqueous suspension comprising the immediate release film coating composition of claim 1 and water.

13. An orally-ingestible substrate coated with the aqueous suspension of claim 12.

14. The coated orally ingestible substrate of claim 13, wherein the immediate release film coating composition disintegrates or dissolves in less than two hours in media with a pH of 1 to 8.

15. An immediate release film coating composition in powder form consisting essentially of:
   a) a polymer selected from the group consisting of hypromellose (hydroxypropyl methylcellulose), hydroxypropyl cellulose, sodium carboxymethyl cellulose, polyvinyl alcohol, copolymers based on polyvinyl alcohol and mixtures thereof;
   b) medium chain glycerides, wherein the medium chain glycerides comprise less than or equal to about 10% of triesters of glycerin; and
   c) a member of the group consisting of glidants, pigments, surfactants and mixtures thereof;
   wherein
   the polymer is present in the amount of 20-70% by weight; and
   the medium chain glycerides are present in the amount of 1-30% by weight.

16. The immediate release film coating composition of claim 15, wherein:
   a) the polymer is present in the amount of 25-60% by weight;
   b) the medium chain glycerides are present in the amount of 2-15% by weight;
   c) the glidant is present in the amount of 4-40% by weight;
   d) the surfactant is present in the amount of 1-4% by weight; and
   e) the pigments are present in the amount of 4-32% by weight.

17. The immediately release film coating composition of claim 16, wherein:
   a) the polymer is present in the amount of 30-50% by weight;
   b) the medium chain glycerides are present in the amount of 3-7% by weight;
   c) the glidant is present in the amount of 10-35% by weight; and
   d) the pigments are present in the amount of 7-30% by weight.

18. The immediate release film coating composition of claim 15, wherein the polymer is polyvinyl alcohol.

19. The immediate release film coating composition of claim 15, wherein the polymer is polyvinyl alcohol, copolymers based on polyvinyl alcohol or a mixture of polyvinyl alcohol and copolymers based on polyvinyl alcohol.

* * * * *